US008757159B2

(12) United States Patent
Nierich

(10) Patent No.: US 8,757,159 B2
(45) Date of Patent: Jun. 24, 2014

(54) APPARATUS AND METHOD FOR SELECTIVE VENTILATION OF A PATIENT

(75) Inventor: Arno Peter Nierich, Hattem (NL)

(73) Assignee: Gelanus B.V., Hattem (NL)

( * ) Notice: Subject to any disclaimer, the term of this patent is extended or adjusted under 35 U.S.C. 154(b) by 617 days.

(21) Appl. No.: 12/532,987

(22) PCT Filed: Apr. 29, 2008

(86) PCT No.: PCT/NL2008/000116
§ 371 (c)(1),
(2), (4) Date: Feb. 1, 2010

(87) PCT Pub. No.: WO2008/136658
PCT Pub. Date: Nov. 13, 2008

(65) Prior Publication Data
US 2010/0147311 A1    Jun. 17, 2010

(30) Foreign Application Priority Data
May 2, 2007   (NL) ...................................... 1033792

(51) Int. Cl.
*A61M 16/00* (2006.01)
(52) U.S. Cl.
USPC .................................................... 128/207.14
(58) Field of Classification Search
USPC ............. 128/207.14, 207.16, 200.24, 207.15, 128/200.26; 604/96.01, 192, 284, 104, 105, 604/106; 606/108, 192; 600/424
See application file for complete search history.

(56) References Cited

U.S. PATENT DOCUMENTS

| 4,840,172 A | 6/1989 | Augustine et al. |
| 6,609,521 B1 | 8/2003 | Belani et al. |
| 2004/0035429 A1 | 2/2004 | Wakabayashi |
| 2004/0144387 A1 | 7/2004 | Amar |

FOREIGN PATENT DOCUMENTS

EP    1407796    4/2004

*Primary Examiner* — Nicholas Lucchesi
*Assistant Examiner* — Brooke Matney
(74) *Attorney, Agent, or Firm* — Bozicevic, Field & Francis LLP; Bret E. Field; Daniel G. Stoddard

(57) ABSTRACT

The invention relates to a device for selective ventilation of one or both lungs of a patient, comprising an endotracheal tube to be arranged in the trachea of the patient and having a proximal and a distal end, an endobronchial tube connected thereto and having a proximal and a distal end, the distal end of which extends beyond the distal end of the endotracheal tube, and means for positioning by feel the distal end of the endobronchial tube in at least a longitudinal direction of the trachea. The positioning means are herein adapted to also position the distal end of the endobronchial tube in a peripheral direction of the trachea. The positioning means can be arranged close to the distal end of the endobronchial tube and can extend so far outside the periphery thereof during use that they come to lie on the carina of the patient. The positioning means can also be asymmetrical relative to the periphery of the endotracheal and/or endobronchial tube and can be adapted for co-action with the trachea wall. The positioning means can comprise a balloon or a resiliently deformable member.

19 Claims, 3 Drawing Sheets

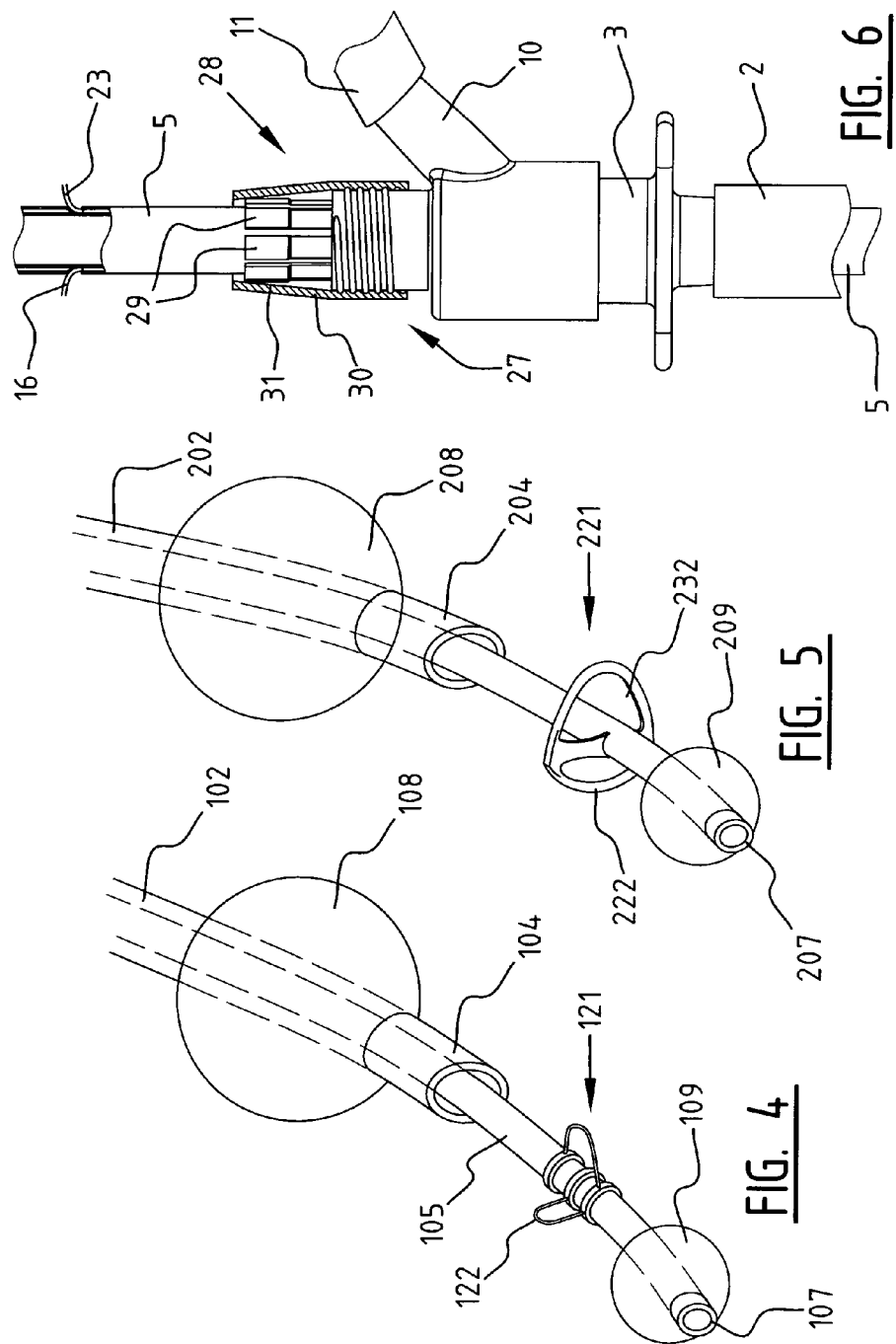

APPARATUS AND METHOD FOR SELECTIVE VENTILATION OF A PATIENT

The invention relates to a device for selective ventilation of one or both lungs of a patient, comprising an endotracheal tube to be arranged in the trachea of the patient and having a proximal and a distal end, an endobronchial tube connected thereto and having a proximal and a distal end, the distal end of which extends beyond the distal end of the endotracheal tube, and means for positioning by feel the distal end of the endobronchial tube in at least longitudinal direction of the trachea. Such a ventilating device is known, for instance from US 2004/0035429 A1.

In thoracic anesthesiology it is necessary in specific operations that the lungs can be respirated or ventilated individually. In most cases this now takes place using a respiratory tube which is provided with a dividing wall whereby two air channels are created, also referred to as a double-lumen respiratory tube. This respiratory tube is usually inserted into the airways through the mouth of the patient. The air outlet of one of the channels is here placed in one of the bronchi, while the air outlet of the other channel, which is shorter, is then situated in the trachea. The windpipe is then closed by inflating a balloon which is arranged around the respiratory tube. The bronchus in which the air outlet of the longer channel is situated is likewise closed by inflating a balloon arranged therearound.

The separation of air channels continues externally of the patient. The air supply can now be regulated using the balloons in the airways and by means of clamps which can be placed on the different tubes externally of the patient. This makes it possible to ventilate both lungs simultaneously or one lung separately.

A variant of this system is described in the above stated document US 2004/0035429 A1. This is a ventilating device consisting of two tube parts coupled releasably to each other; a relatively short tube which is introduced into the trachea of the patient and is referred to as endotracheal tube, and a longer tube which debouches in one of the bronchi of the patient and is thus referred to as endobronchial tube. The endobronchial tube is guided through the endotracheal tube. Around the thus mutually connected tubes can be arranged a balloon with which the trachea can be closed, while the endobronchial part of the endobronchial tube is likewise provided with a balloon with which the relevant bronchus is closed.

This known ventilating device is further provided with means for positioning thereof by feel in longitudinal direction of the trachea so that the endobronchial tube extends to a desired depth into one of the bronchi. These positioning means take the form of a Y-guide which is connected to the endobronchial tube and which comes to lie against the carina. The Y-guide is attached to a spring-loaded stylet which runs along the endobronchial tube, and is itself also resiliently deformable to enable feed through the endotracheal tube.

The problem of selective intubation of a patient using a device with two tubes is that the operation for inserting the tubes cannot be performed accurately. It is a so-called "blind" technique. Positioning may hereby take an unnecessarily long time. The inaccuracy results because it is difficult to position the endobronchial tube in the bronchus without the use of a bronchoscope. The double lumen tube used for the ventilation is in practice now strengthened and pre-curved using a stylet. This can result in damage to the trachea wall. In addition, multiple checks as to whether the respiratory tube is positioned correctly must take place during the intubation using a stethoscope. Such a check must also be carried out after each change in the position of the patient.

Another significant drawback of the conventional ventilating device is that the double lumen respiratory tube has a relatively large diameter and therefore exerts pressure on the wall over the whole length of the trachea. Pressure injury can occur in the trachea wall as a result. The vocal cords can further also be damaged when the double lumen respiratory tube is used for a longer period of time. In order to prevent this the double lumen respiratory tube is in practice often removed after an operation and replaced by a single lumen tube, which exerts less pressure on the trachea wall or the vocal cords. This does however entail the patient having to be intubated again, which is time-consuming and complicated and once again entails the risk of damage. This reintubation can even result in life-threatening situations when the single lumen respiratory tube is not inserted quickly enough.

For the purpose of inserting a ventilating device of the above discussed type use can however be made of a bronchoscope, which must be inserted through a separate connection close to the proximal end of the endotracheal tube, so externally of the patient. With this bronchoscope the position of the endotracheal and endobronchial tubes can be visually monitored, after which the endobronchial tube can be guided to the desired bronchus using a stylet to be inserted into the tubes. In addition to the necessary structural modifications, this therefore also requires a number of additional operations, whereby this surgery is not only expensive but also time-consuming.

These problems are partially resolved by the ventilating device according to the stated document US 2004/0035429 A1. By guiding the tube by feel to a selected depth in the trachea using the positioning means described therein, the distal end of the endobronchial tube can be blindly positioned very accurately at the correct depth in the trachea. The device known from this document has the drawback however that the positioning means are not intended, or even suitable, for positioning the endobronchial tube by feel in the correct bronchus. The Y-shaped positioning means can only indicate the desired depth since they then come up against the carina. It does then however remain unclear into which bronchus the distal end of the endobronchial tube is protruding. In order to nevertheless guide this distal end to some extent, the endobronchial tube is connected in this older document to a preformed stylet with which the distal end is urged in a determined direction. This in turn has the drawback that such a construction is complicated and therefore expensive, and the preforming takes time. The pre-curved endobronchial tube can moreover cause damage to the trachea, whereby the patient may afterwards experience discomfort from the operation.

Also known from U.S. Pat. No. 6,609,521 is a ventilating device, in particular for children, with an endotracheal tube and an endobronchial tube. The endotracheal tube here transposes into the endobronchial tube with a bend, so that it is thus a single-lumen tube. This combined endotracheal and endobronchial tube is also provided with means with which it can be placed by feel in longitudinal direction of the trachea in the form of a foam cushion which comes to lie on the carina. Roughly at the position of the bend the foam cushion is placed eccentrically outside the endobronchial tube, but close enough thereto to fit through the oral cavity, the pharynx, the larynx and the trachea. It thus serves only as a stop for the carina. Just as the ventilating device with the stylet, this device with preformed, bent tube has the drawback that the wall of the trachea can thereby be damaged.

Further known from U.S. Pat. No. 4,840,172 is a ventilating device with a double-lumen endotracheal/endobronchial tube with a separate mechanism for positioning the tube by feel. This positioning mechanism consists of a tripod which is lowered through the tube and then unfolds and engages the carina. After positioning of the tubes on the basis of markings on the rod of the tripod it is once again retracted. This arranging and retracting of the positioning means is complicated and time-consuming, while the number of separate components in the vicinity of the patient is hereby increased unnecessary. In addition, this known device has all the drawbacks of a double-lumen system. Finally, the tripod coming to rest on the carina only provides an indication of the insertion depth of the tubes.

The invention now has for its object to improve a ventilating device of the type described in the preamble such that the above stated problems do not occur, or at least do so to lesser extent. According to the invention this is achieved in such a ventilating device in that the positioning means are adapted to also position the distal end of the endobronchial tube in peripheral direction of the trachea. The endobronchial tube can hereby be blindly positioned very precisely in the desired bronchus. Because the endobronchial tube now does not need to be strengthened or pre-curved using a stylet, time can be saved and no damage is caused to the trachea, whereby the patient will also experience less discomfort from the operation afterwards.

When the positioning means are arranged close to the distal end of the endobronchial tube and extend so far outside the periphery thereof during use that they come to lie on the carina of the patient, the correct insertion depth of the respiratory tube can be established by feel in simple manner through the increase in the resistance when the protruding positioning means come up against the carina, the point of separation of the two bronchi.

The positioning means are preferably asymmetrical relative to the periphery of the endobronchial tube and are adapted for co-action with the trachea wall. The endobronchial tube is hereby urged out of the centre of the trachea so that it can be easily guided along the carina into one of the two bronchi. The positioning means can here take an asymmetrical form, although it is also possible to envisage them being symmetrical per se, but being arranged eccentrically on the endobronchial tube.

In order to be able to manipulate the endobronchial tube externally of the patient such that it is introduced into the desired bronchus, the ventilating device can be provided with means connected to the proximal end of the endobronchial tube for the purpose of directing the distal end thereof.

The endobronchial tube is preferably received in the endotracheal tube. Use can thus be made for the intubation of a standard endotracheal tube instead of a double-lumen tube. The diameter of this endotracheal tube is smaller than that of a double-lumen tube, whereby it does not lie against the trachea wall along the full length, and pressure injury is thus avoided. Furthermore, the endobronchial tube can thus be inserted or removed at any moment during the operation since it only has to be inserted through the already placed endotracheal tube. The positioning of the endobronchial tube is hereby also improved. The separate lung ventilation can also be started in any position of the patient, since the access to the airway is always ensured by the presence of the endotracheal tube. Finally, in the case that a lung must be removed (pneumonectomy), the endobronchial tube can be retracted or removed so that there is no risk of it being entrained with the resection surface of the main bronchus.

In order to enable moving of the positioning means through the endotracheal tube, they are in this case preferably movable between a retracted position, in which they lie closely against the endobronchial tube, and an extended operative position. This can be achieved in simple manner when the positioning means comprise at least one balloon and/or at least one deformable member. In the latter case the positioning member can be resiliently deformable so that it returns automatically to the operative position.

In order to enable the endotracheal and the endobronchial tubes to be held fast in the correct position after the positioning, the ventilating device is preferably provided with means for fixing the endobronchial tube relative to the endotracheal tube.

When these fixing means comprise a clamping mechanism arranged close to the proximal end of the endotracheal tube and engaging on the endobronchial tube, they can be operated externally of the patient in simple manner.

A structurally simple, effective and easy-to-operate clamping mechanism comprises a number of resiliently flexible fingers engaging on the endobronchial tube and a wedge-shaped pressure ring placed therearound.

The invention also relates to a method for selective ventilation of one or both lungs of a patient, comprising of arranging in the trachea of the patient an endotracheal tube with a proximal and a distal end and, connected thereto, an endobronchial tube with a proximal and a distal end, wherein the distal end of the endobronchial tube extends beyond the distal end of the endotracheal tube, and wherein the endobronchial tube is positioned by feel in at least longitudinal direction of the trachea such that the distal end thereof extends into a bronchus of the patient. As already stated above, such a ventilation method is known in different variants.

The invention has for its object to improve this ventilation method such that the above discussed problems do not occur, or at least do so to lesser extent. According to the invention this is achieved in such a ventilation method in that the endobronchial tube is positioned by feel in peripheral direction of the trachea such that the distal end thereof extends into a chosen bronchus of the patient. It is thus possible to dispense with the use of a bronchoscope and stylet, while continuous monitoring using a stethoscope is no longer necessary either.

The invention is now elucidated on the basis of a number of embodiments, wherein reference is made to the accompanying drawing in which corresponding components are designated with reference numerals increased by 100 at a time, and in which:

FIG. 4 is a perspective detail view of a second embodiment of the positioning means;

FIG. 5 is a perspective detail view of a third embodiment of the positioning means; and FIG. 6 is a detail view of the clamping mechanism with which the tubes are fixated relative to each other.

Figure 1:
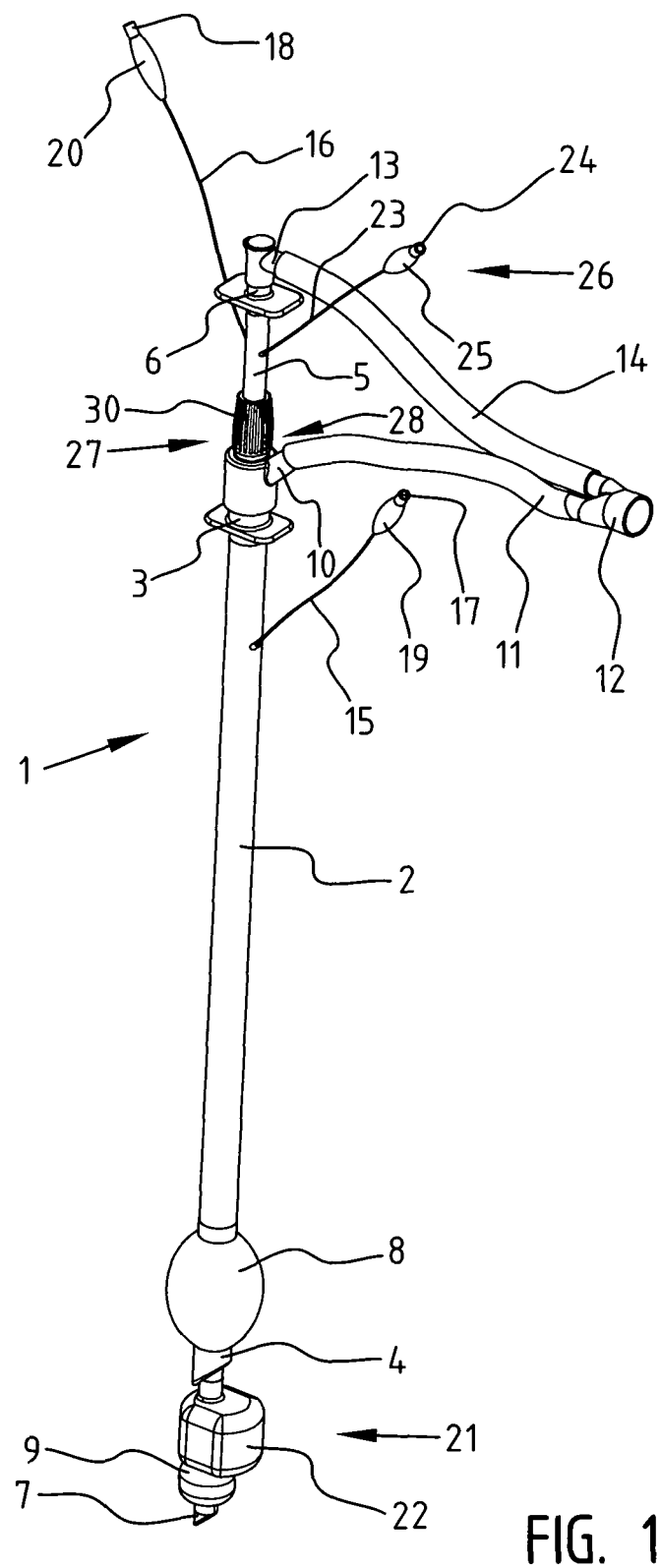
FIG. 1 is a perspective view of the ventilating device according to the invention, wherein the different balloons are inflated.
Figure 2:
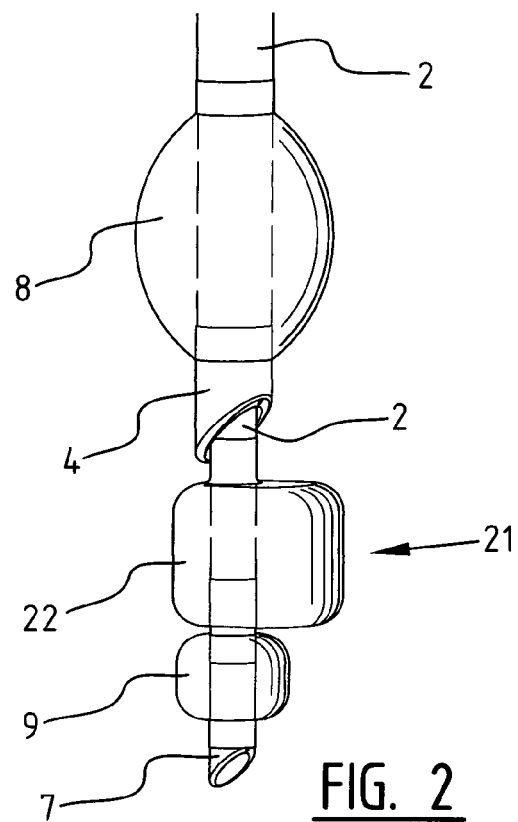
FIG. 2 is a perspective detail view of the distal end of the endotracheal and endobronchial tubes with a first embodiment of the positioning means.
Figure 3:
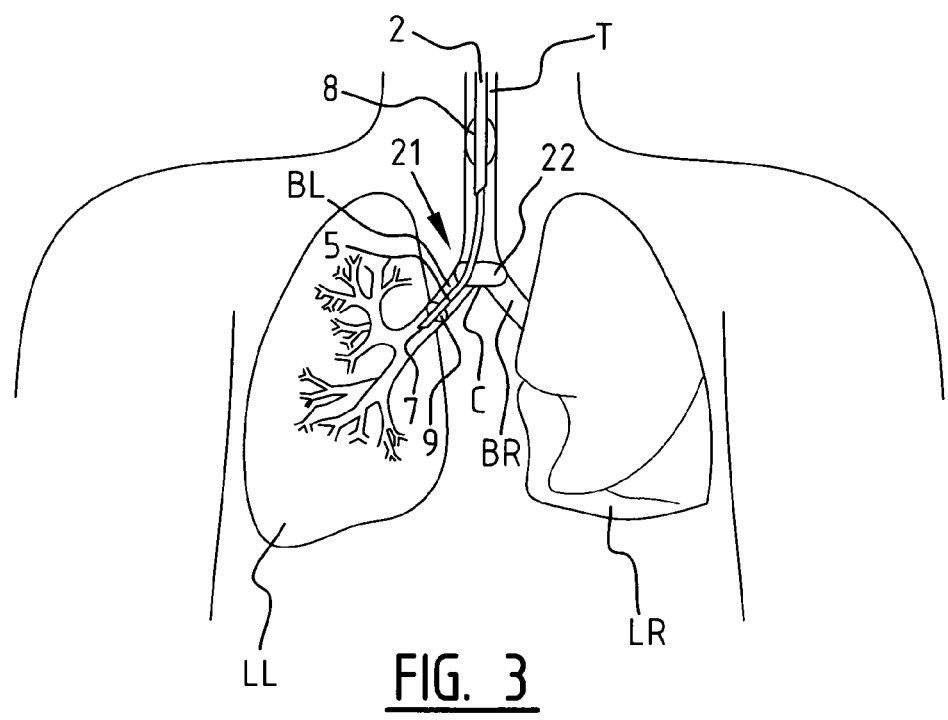
FIG. 3 is a schematic view of the ventilating device in use.

A device 1 for selective ventilation of the left lung LL, the right lung LR or both lungs LL, LR of a patient P comprises an endotracheal tube 2 with a proximal end 3 and a distal end 4 (FIG. 1). Connected to this endotracheal tube 2 is an endobronchial tube 5 which likewise has a proximal end 6 and a distal end 7. Distal end 7 of endobronchial tube 5 extends beyond distal end 4 of endotracheal tube 2. In the shown example endobronchial tube 5 is relatively thin and is received in endotracheal tube 2, which has a larger diameter. This diameter is however still clearly smaller than that of the trachea T of patient P, so that endotracheal tube 2 remains clear of the wall of trachea T (FIG. 3).

As is usual, endotracheal tube 2 is provided with a balloon 8 with which it can be fixed sealingly in trachea T of patient P. Endobronchial tube 5 is likewise provided in conventional manner close to its distal end 7 with a balloon 9, with which it can be fixed sealingly in the left bronchus BL or the right bronchus BR of patient P. Although these balloons are shown in inflated state in all the figures, it will be apparent that they are normally empty before use and are only inflated once ventilating device 1 has been inserted into the patient.

Balloons 8, 9 are connected to connections 17, 18 via thin conduits 15, 16 received respectively in endotracheal tube 2 and endobronchial tube 5. A syringe (not shown here) can be connected by these connections 17, 18 to conduits 15, 16 in order to inflate balloons 8, 9. In order to be able to monitor the degree of filling of balloons 8, 9 externally of patient P, small pilot balloons 19, 20 are also arranged between conduits 15, 16 and connections 17, 18.

Proximal end 3 of endotracheal tube 2 is provided with a connection 10 whereby tube 2 can be connected to a first conduit 11 which leads to a coupling piece 12. This coupling piece 12 can in turn be connected to a respirator machine (not shown here). Proximal end 6 of endobronchial tube 5 is also provided with a connection 13, whereby this tube 5 can be connected to a second conduit 14, which also leads to coupling piece 12. Accommodated in connections 10, 13 or in conduits 11, 14 are valves (not shown) with which the one and/or the other tube 2, 5 can, as desired, be connected to the respirator machine or, conversely, disconnected therefrom. Instead of using such valves for control of the airflow, use could also be made of clamps which are arranged on conduits 11, 14, at least when conduits 11, 14 are sufficiently flexible.

In order to enable simple positioning by feel of endobronchial tube 5 in both longitudinal direction and peripheral direction of trachea T, after it has been fed through endotracheal tube 2, such that distal end 7 thereof extends as desired into one of the bronchi BL, BR of patient P, ventilating device 1 according to the invention is provided with positioning means 21. In the shown example these are arranged close to distal end 7 of endobronchial tube 5 and extend outside the periphery of this tube 5 during use such that they co-act with both the carina C, the point of separation of the two bronchi BL, BR and the wall of the trachea T.

Using these positioning means 21 the correct insertion depth of ventilating device 1 can in the first instance be determined in simple manner by feel. Because positioning means 21 extend outside the periphery of endobronchial tube 5—and in the shown example also outside the periphery of endotracheal tube 2—they will after all come up against carina C. The resistance hereby increases perceptibly, this forming an indication that the correct insertion depth of endobronchial tube 5 has been reached.

Because endobronchial tube 5 is placed through endotracheal tube 2 in the shown example, positioning means 21 must have a retracted position, in which position they can be pressed or pulled through endotracheal tube 2. In the shown example the positioning means take for this purpose the form of a balloon 22 which can be inflated after it has passed distal end 4 of endotracheal tube 2. For this purpose a thin conduit 23 is again provided, with a connection 24 and a pilot balloon 25. The part of conduit 23 protruding outside patient P, connection 24 and pilot balloon 25 serve yet another purpose, which will be elucidated hereinbelow.

In addition, positioning means 21 are adapted to determine the position of the endobronchial tube in peripheral direction of the trachea by co-action with the trachea wall. In the shown example positioning means 21 are placed asymmetrically or eccentrically relative to the periphery of endobronchial tube 5; in top view balloon 22 has the form of an oval, which extends further outside the periphery of tube 5 on one side than on the opposite side. Endobronchial tube 5, which, just as endotracheal tube 2, is manufactured from a relatively flexible material, is hereby pressed out of the centre of the trachea when the asymmetrical or eccentric balloon 22 is inflated and makes contact with the wall of trachea T. This prevents distal end 7 of endobronchial tube 5 running up against carina C, which is after all situated roughly in the middle under trachea T. Because balloon 22 is relatively soft and yielding, the wall of trachea T will otherwise not be damaged thereby.

In order to enable targeted guiding of distal end 7 of endobronchial tube 5 into left bronchus BL or right bronchus BR, ventilating device 1 is further provided with targeting means 26. These targeting means 26 are connected to proximal end 6 of endobronchial tube 5 so that targeting of distal end 7 of tube 5 can take place externally of patient P. There is here a fixed relation, known to the user, between the position of targeting means 26 and the direction of distal end 7 of endobronchial tube 5. In the shown example the part of conduit 23 protruding externally of patient P, connection 24 and pilot balloon 25 function as targeting means 26.

Instead of being inflatable, the positioning means can also be given a deformable form. They can then also be pressed or pulled through endotracheal tube 2 and returned to their extended position when leaving the distal end 4 thereof. Examples of such deformable positioning means 121; 221 are rigid ribs 122 (FIG. 4) or a frame 222 which bounds an opening 232 (FIG. 5). Deformable positioning means 121; 221 are once again asymmetrical or eccentric. In the case of ribs 122 these take a different form on different sides of endobronchial tube 105, while frame 222 also extends further outside endobronchial tube 205 on one side than on the other. Because positioning means 121; 221 are readily deformable, they will not result in damage to the wall of trachea T.

These deformable positioning means 121; 221 can be returned to their extended position by a pull cord or the like connected thereto and trained through endotracheal tube 2. It is however also possible to embody positioning means 121; 221 in resiliently deformable manner, for instance from an elastic material or a material with a shape "memory". In this case positioning means 121; 221 return to the extended position automatically after passing distal end 4 of endotracheal tube 2, and there is of course no need for a filling conduit with connection and pilot balloon as in the first embodiment, nor for any kind of pull cord or other operating mechanism. Targeting means 126; 226 can then be formed in these two embodiments by the part, protruding externally of patient P, of filling conduit 116; 216 for closing balloon 109; 209 at the distal end 107; 207 of endobronchial tube 105; 205. On the other hand, it is also possible in this case to arrange a separate engaging member on proximal end 106; 206 of endobronchial tube 105; 205.

Finally, ventilating device 1 is also provided with means 27 for fixing the endotracheal and endobronchial tubes 2, 5 relative to each other. Using these fixing means 27 the endobronchial tube 5 is secured as soon as distal end 7 thereof has been inserted to the correct depth in the desired bronchus BL, BR. In the shown example fixing means 27 comprise a clamping mechanism 28 which is arranged close to the proximal end 3 of endotracheal tube 2 and which engages on endobronchial tube 5. This clamping mechanism 28 comprises a number of resiliently flexible fingers 29 which engage on endobronchial tube 5 (FIG. 6). Placed round these fingers 29 is a pressure ring 30 which has a wedge-shaped or tapering inner surface 31. Through tightening of ring 30 this inner surface 31 slides over the outer side of fingers 29, which are thereby bent inward and thus firmly fix endobronchial tube 5.

The method according to the invention thus proceeds as follows.

Once the patient P has been anaesthetized, he/she is intubated with endotracheal tube 2 via the mouth or nose. When distal end 4 of endotracheal tube 2 has reached trachea T, balloon 8 can be inflated, whereby trachea T is closed off. Endotracheal tube 2 is secured outside the mouth or nose of the patient with tape in order to fix the position. Balloon 8 also contributes toward fixing of tube 2 in the trachea.

Endobronchial tube 5 is then inserted so far into endotracheal tube 2 that both its distal end 7 with balloon 9 thereon and positioning means 21 extend outside distal end 4 of the endotracheal tube.

Positioning balloon 22 is then inflated which, due to its asymmetrical or eccentric placing relative to endobronchial tube 5, ensures that this tube 5 comes to lie in left bronchus BL or right bronchus BR when it is moved further downward through endotracheal tube 2. Using targeting means 26 the distal end 7 of endobronchial tube 5 is herein rotated in the direction of the desired bronchus BL or BR. When balloon 22 comes up against carina C and the resistance therefore increases, the movement is stopped. Distal end 7 of endobronchial tube 5 will then be situated in one of the bronchi BL, BR at a desired depth, which is determined by the distance from this end 7 to positioning means 21. This depth can thus be varied by arranging positioning means 21 at another location on endobronchial tube 5.

Balloon 9 can subsequently be inflated, whereby the relevant bronchus BL or BR is closed off and both lungs LL, LR are thus isolated from each other and from the mouth and nose of the patient. In this position tubes 2, 5 are fixed relative to each other by means of fixing means 27.

Positioning balloon 22 can then be deflated in order to create space for the airflow through trachea T, and endotracheal tube 2 and endobronchial tube 5 can be connected to the respirator machine by means of conduits 11 and 14 and coupling piece 12.

Finally, the respirator machine can be started and the air supply to and air discharge from one or both lungs LL, LR can be controlled by controlling the valves in conduits 11, 14 or by placing clamps on conduits 11, 14.

When use is made of the resiliently deformable positioning means according to FIG. 4 or 5 instead of balloon 22, the steps of inflating and deflating balloon 22 are dispensed with, whereby intubation will require slightly less time.

The device and method as described above thus make it possible to prepare a patient P in rapid, simple and atraumatic manner for a selective ventilation of one or both lungs LL, LR, without additional operations or monitoring being necessary for this purpose. Using the described ventilating device respiration of the patient P can also continued in simple manner after surgery if this should be necessary. For this purpose the endobronchial tube 5 only need be uncoupled from the respirator machine, after which fixing means 27 can be released and balloon 9 can be deflated. Endobronchial tube 5 can then be pulled out of endotracheal tube 2, after which endotracheal tube 2 can be connected directly to the respirator machine and used for the further respiration. In contrast to the situation where a conventional double-lumen tube is used, it is thus not necessary to completely remove the respiratory tube used during the operation and reintubate patient P with another tube.

Although the invention has been described above on the basis of a number of embodiments, it will be apparent that it is not limited thereto. The form and embodiment of the positioning means could thus be chosen differently than shown here. The connection of the tubes to the ventilating equipment and the mutual attachment of the tubes could also be embodied differently than shown here. The scope of the invention is therefore defined solely by the following claims.

The invention claimed is:

1. A device for selective ventilation of one or both lungs of a patient, comprising:
   an endotracheal tube to be arranged in the trachea of the patient and having a proximal and a distal end,
   an endobronchial tube slidably received in the endotracheal tube and having a proximal and a distal end, the distal end of which extends beyond the distal end of the endotracheal tube, and
   means for positioning by feel the distal end of the endobronchial tube in at least a longitudinal direction of the trachea, wherein the positioning means are adapted to also position the distal end of the endobronchial tube in a peripheral direction of the trachea, and the endobronchial tube extends through the positioning means,
   wherein the positioning means are arranged closer to the distal end than to the proximal end of the endobronchial tube and extend so far outside the periphery thereof during use that they come to lie on the carina of the patient, and wherein the positioning means are asymmetrical about the periphery of the endotracheal and/or endobronchial tube and are adapted for co-action with a part of the trachea wall between the mouth of the patient and the carina of the patient so as to urge the endobronchial tube out of the centre of the trachea.

2. Ventilating device as claimed in claim 1, characterized by targeting means connected to the proximal end of the endobronchial tube for the purpose of directing the distal end thereof.

3. Ventilating device as claimed in claim 1, characterized in that the positioning means are movable between a retracted position, in which they lie closely against the endobronchial tube, and an extended operative position for co-action with the trachea wall.

4. Ventilating device as claimed in claim 3, characterized in that the positioning means comprise at least one balloon.

5. Ventilating device as claimed in claim 3, characterized in that the positioning means comprise at least one deformable member.

6. Ventilating device as claimed in claim 5, characterized in that the positioning member is resiliently deformable.

7. Ventilating device as claimed in claim 1, characterized by means for fixing the endobronchial tube relative to the endotracheal tube.

8. Ventilating device as claimed in claim 7, characterized in that the fixing means comprise a clamping mechanism arranged close to the proximal end of the endotracheal tube and engaging on the endobronchial tube.

9. Ventilating device as claimed in claim 8, characterized in that the clamping mechanism comprises a number of resiliently flexible fingers engaging on the endobronchial tube and a wedge-shaped pressure ring placed therearound.

10. A method for selective ventilation of one or both lungs of a patient, comprising of arranging in the trachea of the patient an endotracheal tube with a proximal and a distal end and inserting an endobronchial tube with a proximal and a distal end through the endotracheal tube into the trachea, wherein the distal end of the endobronchial tube extends beyond the distal end of the endotracheal tube, and wherein the endobronchial tube is positioned by feel in at least a longitudinal direction of the trachea such that the distal end thereof extends into a bronchus of the patient, wherein the endobronchial tube is positioned by feel in a peripheral direction of the trachea such that the distal end thereof extends into a chosen bronchus of the patient, wherein positioning means are arranged closer to the distal end than to the proximal end of the endobronchial tube which extend outside the periphery thereof during use, wherein the endobronchial tube extends through the positioning means, and the endobronchial tube is inserted so far that the positioning means contact the carina of the patient and wherein the positioning means are arranged asymmetrically about the periphery of the endobronchial tube and are adapted for co-action with a part of the trachea wall between the mouth of the patient and the carina of the patient so as to urge the endobronchial tube out of the centre of the trachea, wherein the endobronchial tube is guided into the chosen bronchus of the patient by rotating the positioning means in the trachea.

11. Method as claimed in claim 10, characterized in that the positioning means are rotated in the trachea by operating targeting means connected to the proximal end of the endobronchial tube.

12. Method as claimed in claim 10, characterized in that when the endobronchial tube is inserted through the endotracheal tube the positioning means occupy a retracted position, in which they lie closely against the endobronchial tube, and after passing the distal end of the endotracheal tube are extended to their operative position for co-action with the trachea wall.

13. Method as claimed in claim 12, characterized in that the positioning means comprise at least one balloon which is inflated after passing the distal end of the endotracheal tube.

14. Method as claimed in claim 12, characterized in that: the positioning means comprise at least one deformable member which, after passing the distal end of the endotracheal tube, is returned to its extended operative position.

15. Method as claimed in claim 14, characterized in that the positioning member is resiliently deformable and, after passing the distal end of the endotracheal tube, returns automatically to its extended operative position.

16. Method as claimed in claim 10, characterized in that the endobronchial tube is fixed relative to the endotracheal tube.

17. Method as claimed in claim 16, characterized in that the endobronchial tube is clamped fixedly close to the proximal end of the endotracheal tube.

18. Method as claimed in claim 10, characterized in that the endobronchial tube, the endotracheal tube or both tubes are ventilated as desired.

19. Method as claimed in claim 18, characterized in that the endobronchial tube and the endotracheal tube are both connected via conduits to a respirator machine and the selective ventilation is controlled by operating valves accommodated in these conduits or clamps arranged round the conduits.

\* \* \* \* \*